(12) United States Patent
Park et al.

(10) Patent No.: US 11,007,136 B2
(45) Date of Patent: May 18, 2021

(54) **COSMETIC COMPOSITION FOR WRINKLE REDUCTION CONTAINING GYPENOSIDE ISOLATED FROM *GYNOSTEMMA PENTAPHYLLUM***

(71) Applicant: CELLTRION INC., Incheon (KR)

(72) Inventors: Young Jun Park, Gyeonggi-do (KR); Kee Won Yu, Gyeonggi-do (KR); Jae Hun Kim, Gyeonggi-do (KR); Yeon Sook Kim, Gyeonggi-do (KR); Seung Ki Lee, Incheon (KR); Joo Hyuck Lim, Incheon (KR); Jong Mook Kim, Incheon (KR); Chi Ho Choi, Incheon (KR); Ju Yeon Kim, Incheon (KR); Jung Yun Kim, Seoul (KR); Sung Ho Moon, Gyeonggi-do (KR)

(73) Assignee: CELLTRION, INC., Incheon (KR)

( * ) Notice: Subject to any disclaimer, the term of this patent is extended or adjusted under 35 U.S.C. 154(b) by 247 days.

(21) Appl. No.: 15/735,569

(22) PCT Filed: Jun. 10, 2016

(86) PCT No.: PCT/KR2016/006151
§ 371 (c)(1),
(2) Date: Dec. 11, 2017

(87) PCT Pub. No.: WO2016/200190
PCT Pub. Date: Dec. 15, 2016

(65) Prior Publication Data
US 2019/0110980 A1    Apr. 18, 2019

(30) Foreign Application Priority Data

Jun. 11, 2015 (KR) .................. 10-2015-0082625

(51) Int. Cl.
| | |
|---|---|
| *A61K 36/00* | (2006.01) |
| *A61K 8/9789* | (2017.01) |
| *A61K 8/63* | (2006.01) |
| *A61Q 19/08* | (2006.01) |

(52) U.S. Cl.
CPC .............. *A61K 8/9789* (2017.08); *A61K 8/63* (2013.01); *A61Q 19/08* (2013.01); *A61K 2800/782* (2013.01)

(58) Field of Classification Search
None
See application file for complete search history.

(56) References Cited

U.S. PATENT DOCUMENTS

| | | | | |
|---|---|---|---|---|
| 5,910,308 A * | 6/1999 | D'Jang | ................. | A23L 33/10 |
| | | | | 424/464 |
| 6,168,795 B1 * | 1/2001 | DJang | ................. | A61K 36/424 |
| | | | | 424/729 |
| 2003/0124205 A1 * | 7/2003 | Menon | ................. | A61K 8/97 |
| | | | | 424/727 |
| 2006/0198809 A1 | 9/2006 | Herrel | | |
| 2007/0292537 A1 * | 12/2007 | Jones | ................. | A61K 8/63 |
| | | | | 424/725 |
| 2011/0085996 A1 | 4/2011 | Yeom et al. | | |

FOREIGN PATENT DOCUMENTS

| | | |
|---|---|---|
| CN | 2194725 Y | 4/1995 |
| CN | 1102335 A | 5/1995 |
| CN | 1110132 A | 10/1995 |
| JP | 2003-95858 A | 4/2003 |
| JP | 2007-51091 A | 3/2007 |
| JP | 2008-525462 A | 7/2008 |
| KR | 100667448 | 1/2007 |
| KR | 10-0757175 | 9/2007 |
| KR | 10-0825450 | 4/2008 |
| KR | 10-0844275 | 7/2008 |
| KR | 20130069430 | 6/2013 |
| KR | 20130075962 | 7/2013 |
| WO | WO 2014/193185 A1 | 12/2014 |

OTHER PUBLICATIONS

Razmovski-Naumovski et al. (2005) Phytochemistry Reviews, 4: 197-219. (Year: 2005).*
Cui et al. (1999) Eur. J. Pharma. Sci. 8: 187-191. (Year: 1999).*
Extended European Search Report dated Dec. 19, 2018, in corresponding European Application No. 16807830.1 (7 pages, in English).
Japanese Office Action dated Feb. 5, 2019, in corresponding Japanese Application No. 2017-564640 (5 pages in Japanese, 4 pages in English).
Hong, H. et al., "Enzymatic Biotransformation of Ginsenoside Rb1 and Gypenoside XVII into Ginsenosides Rd and F2 by Recombinant β-glucosidase from Flavobacterium Johnsoniae," J. Ginseng Res. 36:418-424, The Korean Society of Ginseng (2012).

(Continued)

*Primary Examiner* — Russell G Fiebig
(74) *Attorney, Agent, or Firm* — Potomac Law Group, PLLC (57) ABSTRACT

The present invention relates to a cosmetic composition for wrinkle reduction comprising, as an active ingredient, a *Gynostemma pentaphyllum* gypenoside fraction and, more specifically, to a cosmetic composition for wrinkle reduction, wherein the *Gynostemma pentaphyllum* gypenoside fraction includes at least one gypenoside selected from the group consisting of gypenoside UL1, gypenoside UL2, gypenoside UL3, gypenoside UL4, gypenoside UL5, gypenoside UL6, and gypenoside UL7.

3 Claims, 6 Drawing Sheets

(56) References Cited

OTHER PUBLICATIONS

English Translation of International Search Report of PCT/KR2016/006151, WIPO (dated Sep. 20, 2016).
Teng, R.W. et al., "Hydrolytic Reaction of Plant Extracts to Generate Molecular Diversity: New Dammarane Glycosides from the Mild Acid Hydrosylate to Root Saponins of *Panax notoginseng*," *Helv. Chim. Acta*, 87:1270-1278, John Wiley & Sons, Switzerland (2004).

* cited by examiner

*: $p<0.05$ by repeated measures ANOVA, post hoc Bonferroni correction

COSMETIC COMPOSITION FOR WRINKLE REDUCTION CONTAINING GYPENOSIDE ISOLATED FROM *GYNOSTEMMA PENTAPHYLLUM*

TECHNICAL FIELD

The present invention relates to a cosmetic composition for wrinkle reduction comprising a *Gynostemma pentaphyllum* gypenoside fraction as an active ingredient.

BACKGROUND

Collagen occupies most of an extracellular matrix (ECM), which is made in fibroblasts and secreted out of cells, accounts for about 75% of a dry weight of skin and about 90% of a dermal fibrous component, and maintains an elasticity of skin, while carrying out important functions such as playing a role as an intercellular matrix, functioning as a structural support, providing a tensile strength of skin, and the like. A synthesis and degradation of this collagen is appropriately adjusted in vivo. However, as aging progresses, such synthesis of collagen decreases and an expression of a matrix metalloproteinase (MMPs), an enzyme that degrades collagen, increases, thus creating a wrinkle.

There are many types of wrinkle. The wrinkle is divided into a static wrinkle and a dynamic wrinkle according to its characteristics, and also divided into a periorbital wrinkle, a nasolabial fold, etc., according to its locations. Furthermore, there is a transparent wrinkle, etc., which progresses inside the skin, though it is seemingly invisible.

To suppress such wrinkle from being formed, there may be effective methods for inhibiting a creation of the wrinkle, for example, by promoting a production of collagen or inhibiting an expression or activity of collagenase for degrading collagen, elastase for degrading elastin, or MMPs, a various matrix metalloproteinase enzyme. Out of these methods, there have been various ongoing researches on a method for using a substance for promoting the production of collagen.

Ascorbic acid, α-tocopherol, retinol, super oxide dismutase (SOD), etc., have been used as a substance for reducing a skin wrinkle by promoting a production of collagen. However, their physical and chemical stability is remarkably low or their cost is high, so it has been a reality that they could not be used by such an effective amount as to show a substantial effect of reducing a skin wrinkle. Accordingly, there have been continuous research and development on using a natural plant material, which is comparatively inexpensive and has high stability, as a functional wrinkle-reducing cosmetic ingredient. Furthermore, wrinkle-reducing cosmetic ingredients derived from plant materials such as a noni fruit extract (Patent Registration KR 10-0844275), a forsythia fruit extract (Patent Registration KR 10-0825450), a green tea extract (Patent Registration KR 10-0757175), etc., have been developed, too. However, existing natural plant material extracts have a dark color or a strong scent, and happen to show a change in color or odor when being prepared as a cosmetic composition. Thus, there is a problem in that they are difficult to be actually applied to cosmetics.

Meanwhile, *Gynostemma pentaphyllum*, which is also called dolwoe or gyogoram, is a perennial vine of the family cucurbitaceae, growing wild in Korea's southern areas and islands such as Jeju Island, Ulleungdo Island, etc., as well as China and Japan. It naturally grows in forests of mountains or fields. It grows getting tangled by its rhizomes which extend to the side direction and have joints with white hair, or climbs by its tendrils. A tea obtained by drying *Gynostemma pentaphyllum* leaves is generally called a *Gynostemma* tea, which restores functions of internal organs, shows an anti-stress effect and anti-oxidant effect, and is also known to have an effect on asthma, bronchitis, ulcer, etc. Furthermore, *Gynostemma pentaphyllum* has been well-known for its skin care effect and it is also said that women in China and North Korea have drunk dolwoe tea (*Gynostemma pentaphyllum* Makino) from old times to maintain a healthy skin.

DETAILED DESCRIPTION OF THE INVENTION

Technical Problem

As a result of conducting this research to solve a problem of a conventional natural plant material, the present inventors have identified an excellent wrinkle-reducing effect from a *Gynostemma pentaphyllum* gypenoside fraction, which has not been conventionally known as its use for wrinkle reduction. In particular, the present inventors have identified its excellent effect of reducing not only a general wrinkle but also an invisible transparent wrinkle, thus completing the present invention.

Therefore, an object to be solved by the present invention is to provide a cosmetic composition for wrinkle reduction comprising a *Gynostemma pentaphyllum* gypenoside fraction as an active ingredient.

Also, another object to be solved by the present invention is to provide a cosmetic composition for wrinkle reduction comprising at least one gypenoside represented by a following Formula 1 as an active ingredient.

Furthermore, another object to be solved by the present invention is to provide a method for reducing a wrinkle by using the above cosmetic composition.

Technical Solution

To solve the above object, the present invention provides a cosmetic composition for wrinkle reduction comprising a *Gynostemma pentaphyllum* gypenoside fraction as an active ingredient.

In one specific example of the present invention, the present invention provides a cosmetic composition for wrinkle reduction, characterized in that the above *Gynostemma pentaphyllum* gypenoside fraction comprises at least one gypenoside selected from the group consisting of gypenoside UL1, gypenoside UL2, gypenoside UL3, gypenoside UL4, gypenoside UL5, gypenoside UL6 and gypenoside UL7 as defined below:

in the above description, the gypenoside UL1 means $(23\xi)$-3β,20β,21α-trihydroxy-19-oxo-21,23-epoxy-dammar-24-ene-3-O-[α-L-rhamnopyranosyl $(1\rightarrow2)$]-α-L-arabinopyranoside;

the gypenoside UL2 means $(23\xi)$-3β,20β,21α-trihydroxy-19-oxo-21,23-epoxy-dammar-24-ene-3-O-[β-D-glucopyranosyl $(1\rightarrow3)$]-α-L-arabinopyranoside;

the gypenoside UL3 means $(23\xi)$-3β,20β,21α-trihydroxy-21,23-epoxy-dammar-24-ene-3-O-[α-L-rhamnopyranosyl $(1\rightarrow2)$][β-D-xylopyranosyl $(1\rightarrow3)$]-α-L-arabinopyranoside;

the gypenoside UL4 means $(23\xi)$-3β,20β,21α-trihydroxy-19-oxo-21,23-epoxy-dammar-24-ene-3-O-[α-L-rhamnopyranosyl $(1\rightarrow2)$][β-D-xylopyranosyl $(1\rightarrow3)$]-α-L-arabinopyranoside;

the gypenoside UL5 means (23ξ)-3β,20β,21α-trihydroxy-19-oxo-21,23-epoxy-dammar-24-ene-3-O-[α-L-rhamnopyranosyl (1→2)][β-D-glucopyranosyl (1→3)]-α-L-arabinopyranoside;

the gypenoside UL6 means 3β,20S,21-trihydroxy-19-oxo-dammar-24-ene-3-O-[α-L-rhamnopyranosyl (1→2)]{[β-D-xylopyranosyl (1→6)][β-D-glucopyranosyl (1→3)]}-α-L-arabinopyranoside-21-O-β-D-glucopyranoside, and the gypenoside UL7 means 3β,20S-dihydroxy-21-carboxyl-dammar-24-ene-3-O-[α-L-rhamnopyranosyl (1→2)]{[β-D-xylopyranosyl (1→6)][βD-glucopyranosyl (1→3)]}-α-L-arabinopyranoside-21-O-β-D-glucopyranoside.

Figure 1:
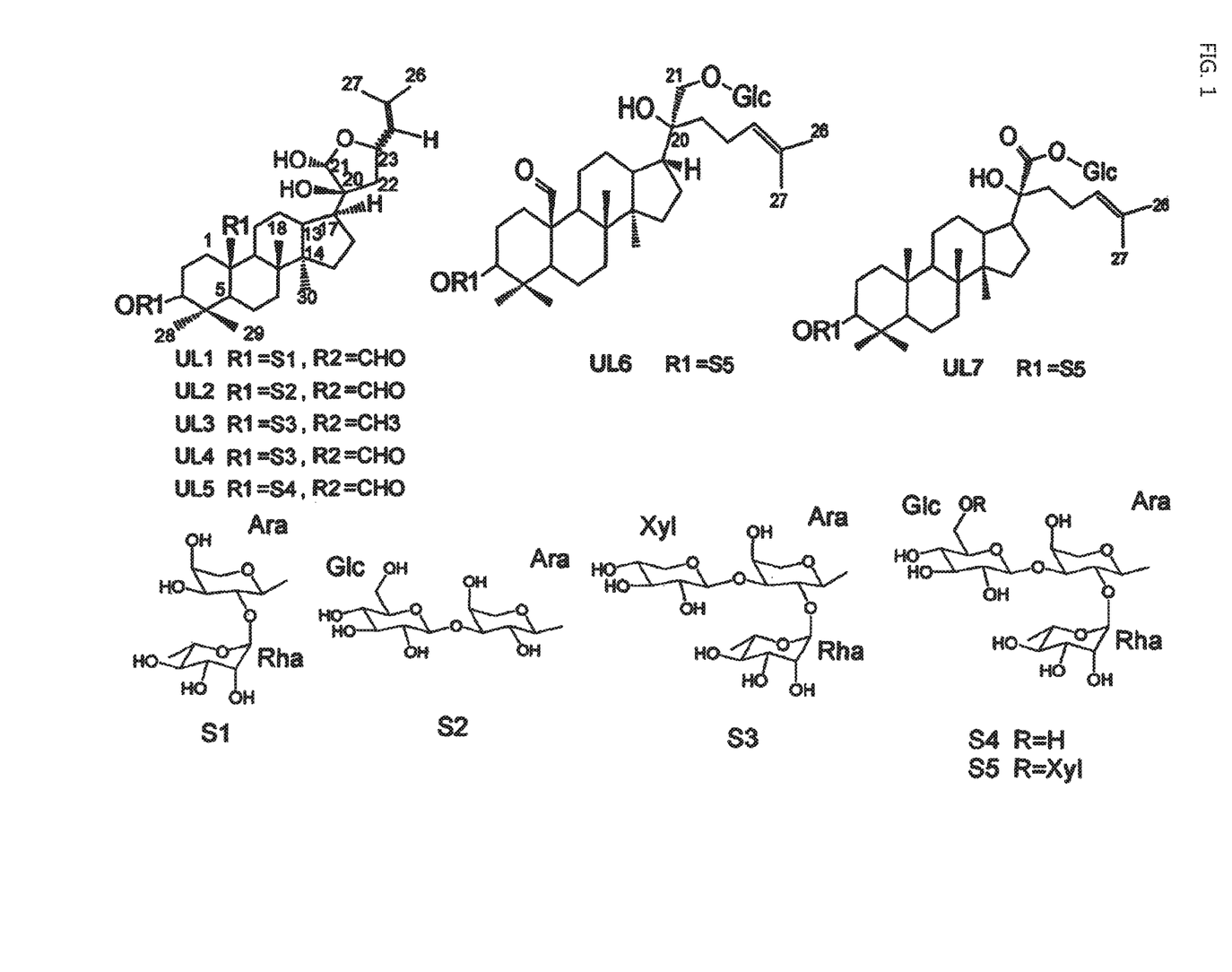
FIG. 1 shows a structural formula of gypenosides UL1 to UL7.

The structural formulas of these above gypenoside UL1, gypenoside UL2, gypenoside UL3, gypenoside UL4, gypenoside UL5, gypenoside UL6 and gypenoside UL7 are such as those shown in FIG. 1.

In one specific example of the present invention, the above *Gynostemma pentaphyllum* gypenoside fraction may be comprised by 0.001 to 30 wt % compared to the total weight of a composition. More particularly, the *Gynostemma pentaphyllum* gypenoside fraction may be comprised by 0.01 to 10 wt % compared to the total weight of the composition.

If a content of the above fraction is less than 0.001 wt %, there does not occur a skin wrinkle-reducing effect. If such content is more than 30 wt %, a degree of increase in the skin wrinkle-reducing effect is insignificant compared to an increase in the content and there is also a problem with stability of formulation as well as low economy.

In one specific example of the present invention, is provided a cosmetic composition for wrinkle reduction, characterized in that the above wrinkle is a transparent wrinkle.

The above transparent wrinkle refers to a wrinkle, which is found in those who do not get wrinkles around eyes in their 20s to early 30s. This skin wrinkle, which is seemingly invisible to naked eyes, but shows a decrease in a dermal density inside a dermal layer, is called a transparent wrinkle. The transparent wrinkle may rapidly progress into a skin wrinkle visible to naked eyes, so it becomes important to take care of the transparent wrinkle.

In another specific example of the present invention, the above *Gynostemma pentaphyllum* gypenoside fraction may comprise at least one of gypenoside UL4 and gypenoside UL5 by 20 to 30 wt % compared to the total weight of the fraction. If the above *Gynostemma pentaphyllum* gypenoside fraction comprises at least one of the gypenoside UL4 and the gypenoside UL5 by less than 20 wt % compared to the total weight of the fraction, there does not occur a skin wrinkle-reducing effect. In case of exceeding 30 wt %, a degree of increase in the skin wrinkle-reducing effect is insignificant compared to a content increase and there is also a problem with stability of formulation as well as low economy.

Furthermore, to solve the above object, the present invention provides a cosmetic composition for wrinkle reduction comprising at least one gypenoside represented by a following Formula 1 as an active ingredient:

<Formula I>

In the above Formula I, $R_1$ is a polysaccharide, in which identical or different saccharides selected from the group consisting of rhamnose, xylose, glucose and arabinose are bonded together via a glycosidic linkage;

$R_2$ is methyl ($CH_3$) or aldehyde (CHO); and $R_3$ is

The above polysaccharide collectively refers to a saccharide in which two or more monosaccharides form one molecule via a glycosidic linkage, and a molecular weight thereof is various ranging from thousands to millions. The polysaccharide may include, but is not limited to, a reserve polysaccharide such as starch or glycogen, a structural polysaccharide such as cellulose or chitin, and the like.

The above monosaccharide may include, but is not limited to, a basic unit, etc., of carbohydrate having a simplest structure, such as rhamnose, fucose, arabinose, xylose, mannose, galactose and glucose, which is not hydrolyzed any more by means of acid, base, enzyme, etc.

The above glycosidic linkage refers to a chemical linkage in which a connection between a carbon of one sugar molecule and that of another sugar molecule is made by means of an oxygen atom. A sugar including aldehyde or ketone forms a cyclic hemiacetal or hemiketal structure in a molecule, and then a resulting hydroxy group, newly emerged by means of forming of this structure, is called an anomer hydroxy group. And then, a linkage occurred during a replacement of this anomer hydroxy group is a glycosidic linkage. An aldehyde-derived glycosidic linkage is called an aldosidic linkage and a ketone-derived glycosidic linkage is called a ketosidic linkage.

The above gypenoside may be one extracted or isolated from *Gynostemma pentaphyllum*, but is not limited thereto.

In one specific example of the present invention, the present invention provides a cosmetic composition for wrinkle reduction, characterized in that the above gypenoside is at least one selected from the group consisting of gypenoside UL1, gypenoside UL2, gypenoside UL3, gypenoside UL4, gypenoside UL5, gypenoside UL6 and gypenoside UL7 as defined below:

In the above description, the gypenoside UL1 means (23ξ)-3β,20β,21α-trihydroxy-19-oxo-21,23-epoxy-dammar-24-ene-3-O-[α-L-rhamnopyranosyl (1→2)]-α-L-arabinopyranoside;

the gypenoside UL2 means (23ξ)-3β,20β,21α-trihydroxy-19-oxo-21,23-epoxy-dammar-24-ene-3-O-[β-D-glucopyranosyl (1→3)]-α-L-arabinopyranoside;

the gypenoside UL3 means (23ξ)-3β,20β,21α-trihydroxy-21,23-epoxy-dammar-24-ene-3-O-[α-L-rhamnopyranosyl (1→2)][β-D-xylopyranosyl (1→3)]-α-L-arabinopyranoside;

the gypenoside UL4 means (23ξ)-3β,20β,21α-trihydroxy-19-oxo-21,23-epoxy-dammar-24-ene-3-O-[α-L-rhamnopyranosyl (1→2)][β-D-xylopyranosyl (1→3)]-α-L-arabinopyranoside;

the gypenoside UL5 means (23ξ)-3β,20β,21α-trihydroxy-19-oxo-21,23-epoxy-dammar-24-ene-3-O-[α-L-rhamnopyranosyl (1→2)][β-D-glucopyranosyl (1→3)]-α-L-arabinopyranoside;

the gypenoside UL6 means 3β,20S,21-trihydroxy-19-oxo-dammar-24-ene-3-O-[α-L-rhamnopyranosyl (1→2)]{[β-D-xylopyranosyl (1→6)][β-D-glucopyranosyl (1→3)]}-α-L-arabinopyranoside-21-O-β-D-glucopyranoside, and the gypenoside UL7 means 3β,20S-dihydroxy-21-carboxyl-dammar-24-ene-3-O-[α-L-rhamnopyranosyl (1→2)]{[β-D-xylopyranosyl (1→6)][βD-glucopyranosyl (1→3)]}-α-L-arabinopyranoside-21-O-β-D-glucopyranoside.

In another specific example of the present invention, the above composition may comprise the above gypenoside by 0.0001 to 30 wt % compared to the total weight of the composition. If the above gypenoside is less than 0.0001 wt % compared to the total weight of the composition, there does not occur a skin wrinkle-reducing effect. In case of exceeding 30 wt %, a degree of increase in the skin wrinkle-reducing effect is insignificant compared to a content increase and there is also a problem with stability of formulation as well as low economy.

In yet another specific example of the present invention, the above composition may comprise at least one of gypenoside UL4 and gypenoside UL5 by 0.0002 to 9 wt % compared to the total weight of the composition. If at least one of the gypenoside UL4 and the gypenoside UL5 is less than 0.0002 wt % compared to the total weight of the composition, there does not occur a skin wrinkle-reducing effect. In case of exceeding 9 wt %, a degree of increase in the skin wrinkle-reducing effect is insignificant compared to a content increase and there is also a problem with stability of formulation as well as low economy.

Furthermore, the present invention provides a method for reducing a wrinkle by using the above cosmetic composition.

Hereinafter, the present invention will be described in more detail.

The above gypenoside may be otherwise referred to as dammarane type saponin, triterpene saponin, gynosaponin, etc., and other names of the gypenoside conventionally used in the art are also included in a scope of the present invention.

The above *Gynostemma pentaphyllum* gypenoside fraction may be prepared according to a method, comprising:

(i) adding a solvent to *Gynostemma pentaphyllum* to get an extract, and then obtaining a filtered crude extract of *Gynostemma pentaphyllum*; and (ii) eluting the above crude extract of *Gynostemma pentaphyllum* by means of an absorbent and then drying a resulting the eluate to obtain a *Gynostemma pentaphyllum* gypenoside fraction.

In the above step (i), the crude extract of *Gynostemma pentaphyllum* may be obtained by means of a method that a mixed solvent of distilled water and ethanol is added by an amount that corresponds to 5 to 20 times of a mass-to-volume ratio of an aerial part (leaf and stem) of a dried/cut *Gynostemma pentaphyllum* to perform a stirring extraction at 50-80° C., after which a filtration is carried out.

In the above step (ii), the *Gynostemma pentaphyllum* gypenoside fraction may be obtained in such a way that the above-obtained ethanol crude extract is absorbed into a column filled with a porous polymer synthetic adsorption resin, after which the same is washed and eluted with a mixed solvent of distilled water and ethanol to obtain an eluate, such that the eluate is dried out.

An extract solvent in the above step (i) and a washing and elution solvent in the step (ii) may be one or two or more of distilled water, ethanol, $C_1$ to $C_4$ lower alcohols, ethylacetate, buthylene glycol and propylene glycol.

A porous polymer synthetic adsorption resin in the above step (ii) may be one or two or more kinds of resin selected from the group consisting of Diaion HP20, HP21 or HP2MG resin.

The *Gynostemma pentaphyllum* gypenoside fraction eluted through the above column may be used for preparing a cosmetic composition, in such a way that the fraction is obtained in a powder type by concentrating the eluate under decompression to evaporate the solvent and then freeze-drying a resulting residue, or the fraction is also obtained in an aqueous solution in a form of constantly maintaining a solid content.

However, a method for preparing a gypenoside according to the present invention is not limited thereto and the above gypenoside may be extracted from other plants than *Gynostemma pentaphyllum* or may be synthesized by means of a general chemical synthesis method.

A raw material of *Gynostemma pentaphyllum* to obtain the above *Gynostemma pentaphyllum* gypenoside fraction may be one grown in Ulleung-gun, Gyeongsangbuk-do, South Korea, but is not limited thereto.

Furthermore, a cosmetic composition of the present invention may contain ingredients conventionally used in a cosmetic composition, for example, conventional adjuvants such as a moisturizer, a ultraviolet ray (UV) absorbent, a UV dispersing agent, vitamins, a plant extract, a skin astringent, an anti-inflammatory, a cell activator, a vasodilator, a blood flow stimulant, and a skin function accelerator, a carrier and the like, in addition to various kinds of additives such as a surfactant, a pH regulator, a coloring, a flavoring, a pigment, a preservative, a germicide, a thickener, an antioxidant, a stabilizer, a solubilizing agent, a metal ion sequestering agent, a refreshing agent, a deodorant, an emulsifier, a solubilizer, etc., but a formulation thereof and additive ingredients are not limited to the above description. Also, the above ingredients may be introduced by an amount generally used in a dermatology field.

Examples of the above surfactant may include, but are not limited to, an anionic surfactant such as higher fatty acid soap, alkyl sulfuric acid ester salt, polyoxyethylene alkyl ether sulphate, alkyl ether phosphoric acid ester salt, N-acylamino acid salt, acyl N-methyl taurine salt, etc.; a cationic surfactant such as alkyltrimethyl ammonium chloride, dialkyl dimethyl ammonium chloride, etc.; an ampholytic surfactant such as alkyl dimethylaminoacetic acid betaine, alkyl amidodimethylaminoacetic acid betaine, 2-alkyl-N-carboxy-N-hydroxyimidazolinium betaine, etc.; and a nonionic surfactant such as a polyoxyethylene type, a polyhydric alcohol ester type, an ethylene oxide/propylene oxide block copolymer, etc. Also, a surfactant, which belongs to a polymeric surfactant or a natural surfactant, may be used without a particular limitation.

The above thickener may be, for example, hydroxymethylcellulose, hydroxyethylcellulose, hydroxypropylcellulose, carboxyvinylpolymer, alkyl-modified carboxyvinyl polymer, polyacrylamide, sodium alginate, propylene glycol alginate, agar, sodium polyacrylate, succinoglucan, dextran, mannan, pectin, gellan gum, carrageenan, hyaluronic acid, polyvinyl alcohol, bentonite, aluminum silicate, magnesium silicate, laponite, hectorite, silicic acid anhydride, etc.

The above preservative may be, for example, ethyl parahydroxybenzoate, salicylic acid, sorbic acid, etc.

The above moisturizer may be, for example, hyaluronic acid, condroitin sulfuric acid, pyrrolidone carboxylic acid salt, polyoxyethylene methyl glucoside, polyoxypropylene methyl glucoside, lecithin, phosphatidylcholine, phosphatidylserine, phosphatidylglycerol, phosphatidylinositol, sphingophospholipid and the like.

The above metal ion sequestering agent may be, for example, ethylenediamine tetraacetic acid disodium, edetic acid, edetic acid salt like edetic acid sodium salt, etc., and the like.

The above emulsifier may be, for example, hydrocarbon such as squalene, liquid paraffin, vaseline, solid paraffin, etc.; oil and fat such as olive oil, almond oil, cacao fat, castor oil, etc.; lead such as wax, lanolin, jojoba, etc.; fatty acid such as stearic acid, oleic acid, palmaitic acid, etc.; higher alcohol such as cetanol, stearyle alcohol, etc.; ester such as IPM, glycerin triester, pentaerythritol tetra-ester, etc; and silicone oil such as polysiloxanes, etc.

The above solubilizer may be, for example, propylene glycol fatty acid esters such as glycerin fatty acid ester, polyglycerin fatty acid ester, sorbitan fatty acid ester, propylene glycol monostearate and the like, polyhydric alcohol such as glycerin, diglycerin, ethylene glycol, propylene glycol, 1,3-butylene glycol, etc. and the like.

Examples of the above flavoring may include, but are not limited to, a vegetable flavoring isolated from flowers, leaves, branches, fruit skin, etc.; an animal flavoring such as musk, civet, etc.; hydrocarbons such as monoterpene, etc.; alcohols such as aliphatic alcohol, aromatic alcohol, etc.; aldehydes such as terpene aldehyde, aromatic aldehyde, etc.; ketones such as alicyclic ketone, etc.; esters such as terpene-based ester, etc.; lactones; phenols; oxides; nitrogen containing compounds; acetals, etc. Also, other natural flavoring or synthetic flavoring than the above examples may be used without a particular limitation.

A cosmetic composition of the present invention may be prepared as any formulation conventionally prepared in the art, wherein as one specific example for the cosmetic composition, this may be, but is not limited to, one formulation selected from the group consisting of high viscosity emulsified formulations, low viscosity emulsified formulations and solubilized formulations, and wherein the inventive cosmetic composition may also contain blend ingredients therefor conventionally used in the technical field, to which the present invention pertains, depending on the formulation to be prepared. As one example for the cosmetic composition, this may be formulated into solution, suspension, emulsion, paste, gel, cream, lotion, powder, soap, surfactant-containing cleansing, oil, powder foundation, emulsion foundation, wax foundation, pack, massage cream, spray, and the like, but is not limited thereto. More particularly, the cosmetic composition may be prepared as a formulation such as skin lotion, nutrition lotion, nutrition cream, massage cream, essence, eye cream, sun lotion, sun cream, makeup base, blemish balm (BB) cream, cleansing cream, cleansing foam, cleansing water, pack, a stick-phase product, a balm type product, spray or powder, wherein a water-phase ingredient, an oil-phase ingredient, a surfactant, a moisturizer, a lower alcohol, a thickener, a chelation agent, antiseptic, flavoring, etc., may be additionally selected, blended with each other, added to the cosmetic composition, depending on the formulation to be prepared.

In the cosmetic composition of the present invention, if a formulation is paste, cream or gel, a carrier ingredient may be animal oil, vegetable oil, wax, paraffin, starch, tragacanth, cellulose derivative, polyethylene glycol, silicon, bentonite, silica, talc, zinc oxide or the like.

In the cosmetic composition of the present invention, if a formulation is solution or emulsion, a carrier ingredient may be solvent, solubilizing agent or demulsifier. As one example for the carrier ingredient, this may be water, ethanol, isopropanol, ethyl carbonate, ethyl acetate, benzyl alcohol, benzyl benzoate, propylene glycol, 1,3-butylene glycol oil, glycerol aliphatic ester, polyethylene glycol or sorbitan fatty acid ester.

In the cosmetic composition of the present invention, if a formulation is a suspension, a carrier ingredient may be a liquid-phase diluent such as water, ethanol or propylene glycol: a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth or the like.

In the cosmetic composition of the present invention, if a formulation is powder or spray, a carrier ingredient may be lactose, talc, silica, aluminum hydroxide, calcium silicate or polyamide powder. Particularly, in case of being spray, the cosmetic composition may further contain a propellant such as chlorofluorohydrocarbon, propane/butane or dimethyl ether.

In the cosmetic composition of the present invention, if a formulation is a surfactant-containing cleansing, a carrier ingredient may be aliphatic alcohol sulfate, aliphatic alcohol ether sulfate, sulfosuccinate monoester, isethionate, imidazolinium derivative, sarcosinate, fatty acid amid ether sulfate, alkyl amido betaine, aliphatic alcohol, fatty acid glyceride, fatty acid diethanol amide, vegetable oil, lanolin derivative, ethoxylated glycerol fatty acid ester, or the like.

In the cosmetic composition of the present invention, if a formulation is a surfactant-containing cleansing one, a surfactant-free cleansing one or soap, the cosmetic composition may be applied to skin, and then wiped out, torn off or washed away with water. As one example for the above soap, this may be liquid soap, powder soap, solid soap and oil soap. As one example for the above surfactant-containing cleaning formulation, this may be cleansing foam, cleansing water, cleansing towel and cleansing pack. And, as one example for the above surfactant-free cleansing formulation, this may be cleansing cream, cleansing lotion, cleansing water and cleansing gel, but is not limited thereto.

The cosmetic composition according to the present invention comprises a *Gynostemma pentaphyllum* gypenoside fraction, thus having an excellent effect on reducing a wrinkle, enhancing a skin elasticity and improving a skin dermal density.

More particularly, it was identified that the *Gynostemma pentaphyllum* gypenoside fraction of the present invention promotes a production of procollagen, thus having an excellent effect on reducing a wrinkle, enhancing a skin elasticity and improving a skin dermal density.

The above *Gynostemma pentaphyllum* gypenoside fraction does not cause a side effect to skin, is safe without an irritation, and has an excellent stability of an active ingredient in various storage conditions.

The above *Gynostemma pentaphyllum* gypenoside fraction does not have a change in color, but constantly maintains a content of an active ingredient, even if it is stored under a high temperature or sunlight for a long period of time.

Advantageous Effects

A cosmetic composition comprising an inventive *Gynostemma pentaphyllum* gypenoside fraction as an active ingredient has an excellent wrinkle-reducing effect.

MODE FOR INVENTION

Hereinafter, the present invention will be described in more detail through examples, comparative examples and experimental examples. The following examples and experimental examples are set forth just as the illustrative description of the present invention, but are not to be construed to limit the scope of the present invention.

Example 1. Preparing of a *Gynostemma pentaphyllum* Gypenoside Fraction

1) Preparing of an Ethanol Crude Extract of *Gynostemma pentaphyllum*

1.0 kg of an aerial part (leaf and stem) of a dried *Gynostemma pentaphyllum* was cut/ground, 14 L of 40% ethanol obtained by mixing distilled water and ethanol at a volume ratio of 6:4 was added thereto, and a resulting mixture was stirred at 80° C. for four hours to get an extract, such that the resulting extract was flowed out to get a first extract. Again, 11 L of the same solvent was added to an extractor in which an extraction residue remained, and a resulting mixture was extracted at the same temperature for two hours to flow out an extract and get a second extract, such that the resulting second extract was combined with the first extract. Lastly, the first and second extracts were filtered and concentrated to get an ethanol crude extract of the *Gynostemma pentaphyllum*.

2) Preparing of a *Gynostemma pentaphyllum* Gypenoside Fraction

A column was filled with HP-20, a porous synthetic absorbent, and 40% ethanol was added thereto to keep a balance, such that the ethanol crude extract of the *Gynostemma pentaphyllum* obtained from the Example 14) was diluted with 40% ethanol to slowly carry out loading. After that, 45% ethanol was sufficiently added thereto to remove impurities therefrom, and then a resulting solution was eluted with 80% ethanol to get a *Gynostemma pentaphyllum* gypenoside fraction. A resulting eluate was concentrated under decompression to evaporate ethanol, and a resulting residue was freeze-dried to obtain about 30 g of the *Gynostemma pentaphyllum* gypenoside fraction in a powder type.

Example 2, Isolating and Identification of an Active Ingredient from the *Gynostemma pentaphyllum* Gypenoside Fraction Isolation of an active ingredient from the *Gynostemma pentaphyllum* gypenoside fraction obtained from the Example 1 was performed as follows. 21 g of the *Gynostemma pentaphyllum* gypenoside fraction obtained from the Example 1 was taken out and put into a column (4.6 cm in diameter×31 cm in height) using 323 g of silica gel, and a chromatography was performed by sequentially using 2 L of a mixed solvent of chloroform and methanol at a 8:1 (v/v) mixing ratio, 3 L of the same at a 5:1 (v/v) mixing ratio, 2 L of the same at a 3:1 (v/v) mixing ratio, and 3 L of the same at a 1:1 (v/v) mixing ratio, respectively. Fr. A (1.56 g) (8:1 mixed solvent), Fr. B (5.99 g) (5:1 mixed solvent), Fr. C (3.12 g) (3:1 mixed solvent) and Fr. D (8.15 g) (1:1 mixed solvent) were obtained through the above four kinds of mixed solvent. A chromatography was performed with each fraction in an MCI-gel by gradually raising a concentration of acetonitrile aqueous solution up to 5, 10, 15, 20 and 25%, thus obtaining gypenosides UL1 and UL2 from the Fr. A, gypenosides UL3 and UL4 from the Fr. B, gypenoside UL5 from the Fr. C, and gypenosides UL6 and UL7 from the Fr. D, respectively.

The structural formulas of the above gypenosides UL1, UL2, UL3, UL4, UL5, UL6 and UL7 are such as those illustrated in FIG. 1.

Example 3. Chromatogram Analysis of the *Gynostemma pentaphyllum* Gypenoside Fraction The *Gynostemma pentaphyllum* gypenoside fraction obtained through the Example 1 was analyzed by means of HPLC. The gypenosides UL1 to UL7, identified through the above Example 2, were indicated on a HPLC chromatogram, which were shown in FIG. 2.

Figure 2:
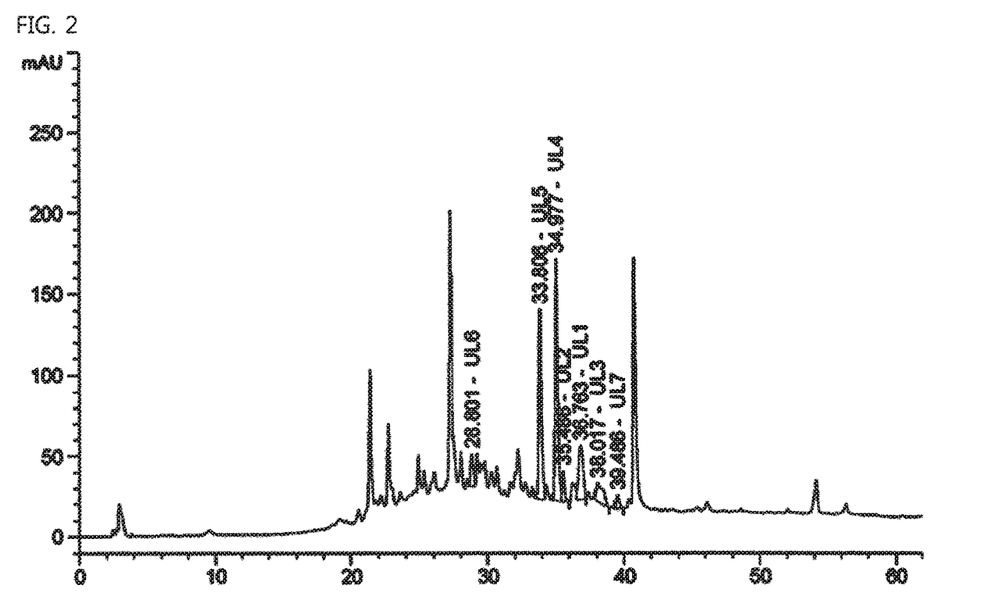
FIG. 2 shows a chromatogram in which a *Gynostemma pentaphyllum* gypenoside fraction is analyzed by means of HPLC-UVD.

As shown in FIG. 2, it was identified that the gypenosides UL4 and UL5 could be isolated with a high content and a high purity unlike the gypenosides UL1, UL2, UL3, UL6 and UL7.

Example 4. Identification of Contents of the Gypenosides UL4 and UL5 from the *Gynostemma pentaphyllum* Gypenoside Fraction As a result of analyzing the *Gynostemma pentaphyllum* gypenoside fraction obtained through the Example 1 with HPLC-UVD 203 nm under a concentration gradient condition of acetonitrile and distilled water by using a C18 column having a diameter of 4.6 mm and a length of 25 cm, it was found that the *Gynostemma pentaphyllum* gypenoside fraction obtained through the Example 1 comprised 121 mg of the gypenoside UL4 and 95.6 mg of the gypenoside UL5 per 1 g of powder.

Experimental Example 1. Effect of the *Gynostemma pentaphyllum* Gypenoside Fraction on Promoting Collagen Synthesis A human dermal fibroblast neonatal (Cascade Co.) was inoculated into a 24-well microplate ($5 \times 10^4$ cells/well) by using a medium, in which Dulbeco's Modified Eagle's Medium (DMEM) was supplemented with 10% fetal bovine serum, thus being cultured under a condition of 37° C. and 5% $CO_2$ for 24 hours. Then, the same was replaced with a serum-free DMEM medium and cultured for 24 hours, after which an appropriate amount of a sample fluid was treated so that a final concentration of each test compound could reach 1 µg/ml and 5 µg/ml. After being cultured for 48 hours, a cell culture fluid was collected and then an amount of procollagen was measured by using a collagen measurement kit of Takara Company (Takara Shuzo Co., Ltd.). First of all, the collected cell culture fluid was injected into a 96-well microplate, to which a primary collagen antibody was evenly applied, such that an antigen-antibody reaction could occur at 37° C. for three hours. The cell culture fluid was removed from the well and washed four times with PBS. A color causing material was injected into each well, after which a reaction took place at a room temperature for 15 minutes, such that 1 N sulfuric acid solution was added thereto, thus stopping the reaction. An optical density was measured at a wavelength of 450 nm by means of a spectrophotometer. A standard curve was drawn by using a standard solution, and the optical density obtained by means of the above method was assigned to the standard curve, thus calculating an amount of procollagen produced from the cell culture fluid, to which each test compound was added.

Results of experimenting on the procollagen-producing effects of the *Gynostemma pentaphyllum* gypenoside fraction obtained from the Example 1, the gypenosides UL4 and UL5 isolated therefrom, and N-acetyl glucosamine (hereinafter NAG), which is a positive control group known to have a skin wrinkle-reducing effect, were indicated in FIG. 3.

Figure 3:
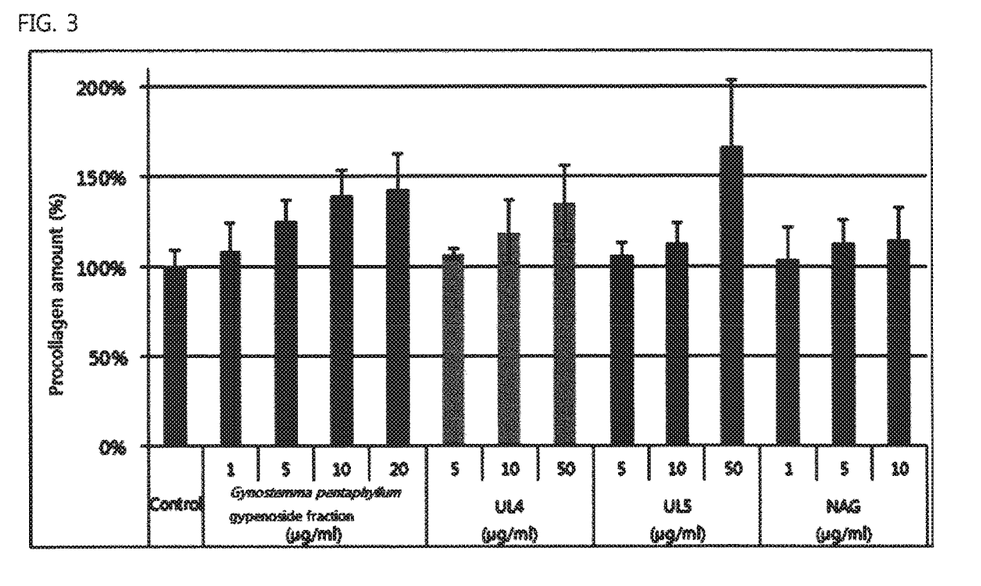
FIG. 3 shows experimental results on procollagen-producing effects of the *Gynostemma pentaphyllum* gypenoside fraction, the gypenosides UL4 and UL5 isolated therefrom, and N-acetyl glucosamine (NAG) as a positive control group.

As shown in FIG. 3, when the procollagen-producing effects of the *Gynostemma pentaphyllum* gypenoside fraction and the gypenosides UL4 and UL5 isolated therefrom were compared with the procollagen-producing effect of the NAG as the positive control group, it was identified that the former ones produced the same or larger amount of procollagen than the latter one at the same concentration, thus showing the same or more excellent procollagen-producing effect.

Experimental Example 2. Safety of the *Gynostemma pentaphyllum* Gypenoside Fraction 1) Cytotoxicity Test A human dermal fibroblast neonatal (Cascade Co.) was inoculated into a 24-well microplate ($5 \times 10^4$ cells/well) by using a medium, in which Dulbeco's Modified Eagle's Medium (DMEM) was supplemented with 10% fetal bovine serum, thus being cultured under a condition of 37° C. and 5% $CO_2$ for 24 hours. Then, the same was replaced with a serum-free DMEM medium and cultured for 24 hours, thus treating the *Gynostemma pentaphyllum* gypenoside fraction obtained from the Example 1 and the gypenosides UL4 and UL5 isolated therefrom, respectively. After being cultured for 48 hours, an MTT solution was added thereto, thus being cultured for four hours. The medium was removed therefrom and DMSO was added thereto, thus dissolving an MTT formazan. The MTT formazan dissolved in the DMSO was taken out and an optical density thereof was measured at 570 nm, thus being compared to a group without sample treatment and indicated as % control.

Figure 4:
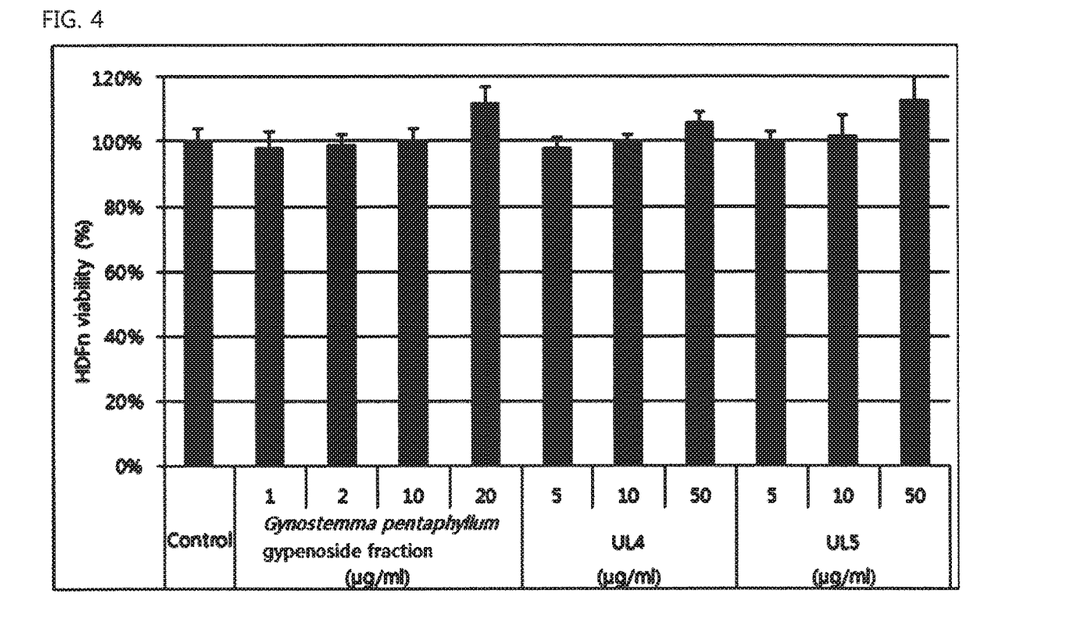
FIG. 4 shows experimental results on cytotoxicity to see safety of the *Gynostemma pentaphyllum* gypenoside fraction.

As shown in a following Table 1 and FIG. 4, it was identified that the *Gynostemma pentaphyllum* gypenoside fraction and the gypenosides UL4 and UL5 isolated therefrom did not show any cytotoxicity at a concentration, at which they showed an effect of promoting a procollagen synthesis.

TABLE 1

| Sample | Treatment Concentration (ug/ml) | HDFn Viability (%) |
|---|---|---|
| *Gynostemma pentaphyllum* gypenoside fraction | 1 | 98 |
| | 5 | 99 |
| | 10 | 100 |
| | 20 | 112 |
| Gypenoside UL4 | 5 | 98 |
| | 10 | 100 |
| | 50 | 106 |
| Gypenoside UL5 | 5 | 100 |
| | 10 | 102 |
| | 50 | 113 |

2) Skin Irritation Test

An irritation test on human skin was performed to identify a skin irritation of a *Gynostemma pentaphyllum* gypenoside fraction, particularly in such a way that a 5×20 cm patch with a certain amount of aqueous solution (20 µl) comprising 0.2, 0.4 and 1.0% of the *Gynostemma pentaphyllum* gypenoside fraction was applied onto each back of 30 adults for 24 hours. Then, the patch was removed therefrom to check a change in skin conditions with naked eyes in one, two and six days later, and results thereof were indicated in Table 2. At that time, a degree of change in skin conditions was classified and evaluated according to following evaluation criteria for skin conditions.

As shown in a following Table 2, it was identified that the *Gynostemma pentaphyllum* gypenoside fraction did not irritate skin at a concentration of 0.2, 0.4 and 1.0%.

<Evaluation Criteria for Skin Conditions>
−: Non irritation
±: Mild irritation
+: Moderate irritation
++: Severe irritation

TABLE 2

| | | | 0.2% | | | 0.4% | | | 1.0% | | |
|---|---|---|---|---|---|---|---|---|---|---|---|
| No. | Age | Sex | 1 day | 2 days | 6 days | 1 day | 2 days | 6 days | 1 day | 2 days | 6 days |
| 1 | 31 | F | — | — | — | — | — | — | — | — | — |
| 2 | 49 | F | — | — | — | — | — | — | — | — | — |
| 3 | 49 | F | — | — | — | — | — | — | — | — | — |
| 4 | 55 | F | — | — | — | — | — | — | — | — | — |
| 5 | 43 | F | — | — | — | — | — | — | — | — | — |
| 6 | 33 | F | — | — | — | — | — | — | — | — | — |
| 7 | 55 | F | — | — | — | — | — | — | — | — | — |
| 8 | 43 | F | — | — | — | — | — | — | — | — | — |
| 9 | 43 | F | — | — | — | — | — | — | — | — | — |
| 10 | 50 | F | — | — | — | — | — | — | — | — | — |
| 11 | 24 | F | — | — | — | — | — | — | — | — | — |
| 12 | 54 | F | — | — | — | — | — | — | — | — | — |
| 13 | 42 | F | — | — | — | — | — | — | — | — | — |
| 14 | 42 | F | — | — | — | — | — | — | — | — | — |
| 15 | 45 | F | — | — | — | — | — | — | — | — | — |
| 16 | 53 | F | — | — | — | — | — | — | — | — | — |
| 17 | 48 | F | — | — | — | — | — | — | — | — | — |
| 18 | 51 | F | — | — | — | — | — | — | — | — | — |
| 19 | 51 | F | — | — | — | — | — | — | — | — | — |
| 20 | 26 | F | — | — | — | — | — | — | — | — | — |
| 21 | 46 | F | — | — | — | — | — | — | — | — | — |
| 22 | 55 | F | — | — | — | — | — | — | — | — | — |
| 23 | 51 | F | — | — | — | — | — | — | — | — | — |
| 24 | 54 | F | — | — | — | — | — | — | — | — | — |
| 25 | 35 | F | — | — | — | — | — | — | — | — | — |
| 26 | 39 | F | — | — | — | — | — | — | — | — | — |
| 27 | 36 | F | — | — | — | — | — | — | — | — | — |
| 28 | 34 | F | — | — | — | — | — | — | — | — | — |
| 29 | 28 | F | — | — | — | — | — | — | — | — | — |
| 30 | 39 | F | — | — | — | — | — | — | — | — | — |
| Mean score | | | 0.00 | | | 0.00 | | | 0.00 | | |
| Judgment | | | No irritation | | | No irritation | | | No irritation | | |

Experimental Example 3. Stability of the *Gynostemma pentaphyllum* Gypenoside Fraction A solution obtained by dissolving powder of the *Gynostemma pentaphyllum* gypenoside fraction at a concentration of 4% in 100 mL of a mixed solvent of propylene glycol, glycerin and distilled water at a ratio of 5:3:2 was used to identify stability of the *Gynostemma pentaphyllum* gypenoside fraction in a raw material state. While the solution was being stored under a condition of 4° C., 30° C. and 45° C. and sunlight for 12 weeks, changes with passage of time (% compared to an initial content) in the gypenosides UL4 and UL5, which were index ingredients for quantification out of the *Gynostemma pentaphyllum* gypenosides, were observed through an HPLC analysis and results thereof were indicated in Table 3.

As shown in a following Table 3, it was identified that the *Gynostemma pentaphyllum* gypenoside fraction had an excellent stability in a raw material state by maintaining at least 90% titer of the gypenosides UL4 and UL5 for 12 weeks under sunlight and high temperature conditions.

TABLE 3

| Elapsed time (week) | Raw material solution of the *Gynostemma pentaphyllum* gypenoside fraction (%) | | | | | | | |
|---|---|---|---|---|---|---|---|---|
| | Gypenoside UL4 | | | | Gypenoside UL5 | | | |
| | 4° C. | 30° C. | 45° C. | Sunlight | 4° C. | 30° C. | 45° C. | Sunlight |
| 1 | 100.2 | 102.8 | 97.1 | 97.6 | 98.8 | 101.8 | 97.6 | 101.1 |
| 2 | 98.1 | 99.9 | 96.3 | 96.6 | 101.3 | 98.2 | 97.5 | 98.4 |
| 4 | 96.9 | 98.7 | 102.7 | 96.6 | 97 | 99 | 96.9 | 98.8 |
| 8 | 98.3 | 96.5 | 97.5 | 98.1 | 97.9 | 101.2 | 99.2 | 97.2 |
| 12 | 96.1 | 96.6 | 102.4 | 97.1 | 98.1 | 102.9 | 103.8 | 97.8 |
| Results | Stable | Stable | Stable | Stable | Stable | Stable | Stable | Stable |

Preparing Example: Cosmetic Composition Comprising the *Gynostemma pentaphyllum* Gypenoside Fraction Based on the above Experimental Example, a cosmetic composition of various formulations, comprising the *Gynos-*

*temma pentaphyllum* gypenoside fraction obtained from Example 1, was prepared according to compositions described in following Tables 4 to 6. Following formulation examples are illustrated by way of example for describing the present invention in more detail and the present invention is not limited to the following examples.

Formulation Example 1. Preparing of a High Viscosity Emulsified Formulation

A prescription for a high viscosity emulsified formulation comprising the *Gynostemma pentaphyllum* gypenoside fraction is such as that shown in Table 4.

TABLE 4

| Phase | Ingredient | Content (%) |
| --- | --- | --- |
| Water phase | Purified water | To 100 |
|  | Moisturizing ingredient | 10-25 |
|  | Thickener | Suitable amount |
|  | Metal ion sequestering agent | Suitable amount |
| Oil phase | PEG-100 Stearate | 0.1-2 |
|  | Glyceryl Stearate | 0.1-2 |
|  | Polysorbate 60 | 0.1-2 |
|  | Stearic Acid | 0.1-2 |
|  | Cetearyl Alcohol | 0.1-2 |
|  | Capric/Caprylic Triglyceride | 10-30 |
|  | Tocopheryl Acetate | 0.1-0.5 |
| Additional I | *Gynostemma pentaphyllum* gypenoside fraction | 0.20 |
| Additional II | Fragrance | Suitable amount |
|  | Preservative | Suitable amount |
|  | Other additive | Suitable amount |

<Method for Preparing a High Viscosity Emulsified Formulation>

① Water and oil phases were respectively heated to be evenly mixed and dissolved.

② The oil phase was inserted into the water phase at 75° C. to mixed and solubilized together.

③ An additional phase I, in which a *Gynostemma pentaphyllum* gypenoside fraction was dissolved, was inserted into a resulting mixture at 50° C. and mixed together, after which an additional phase II was mixed therein together.

Formulation Example 2. Preparing of a Low Viscosity Emulsified Formulation

A prescription for a low viscosity emulsified formulation comprising the *Gynostemma pentaphyllum* gypenoside fraction is such as that shown in Table 5.

TABLE 5

| Phase | Ingredient | Content (%) |
| --- | --- | --- |
| Water phase | Purified water | To 100 |
|  | Ceteareth-6 olivate | 0.1-3 |
|  | Moisturizing ingredient | 10-25 |
|  | Thickener | Suitable amount |
|  | Metal ion sequestering agent | Suitable amount |
| Oil phase | PEG-100 Stearate | 0.1-1 |
|  | Glyceryl Stearate | 0.1-1 |
|  | Polysorbate 60 | 0.1-1 |
|  | Cetyl alcohol | 0.1-1 |
|  | Behenyl alcohol | 0.1-1 |
|  | Squalane | 5-20 |
|  | Tocopheryl Acetate | 0.1-0.5 |
| Additional I | *Gynostemma pentaphyllum* gypenoside fraction | 0.20 |

TABLE 5-continued

| Phase | Ingredient | Content (%) |
| --- | --- | --- |
| Additional II | Fragrance | Suitable amount |
|  | Preservative | Suitable amount |
|  | Other additive | Suitable amount |

<Method for Preparing a Low Viscosity Emulsified Formulation>

① Water and oil phases were respectively heated to be evenly mixed and dissolved.

② The oil phase was inserted into the water phase at 75° C. to mixed and solubilized together.

③ An additional phase I, in which a *Gynostemma pentaphyllum* gypenoside fraction was dissolved, was inserted into a resulting mixture at 50° C. and mixed together, after which an additional phase II was mixed therein together.

Formulation Example 3. Preparing of a Solubilized Formulation

A prescription for a solubilized formulation comprising the *Gynostemma pentaphyllum* gypenoside fraction is such as that shown in Table 6.

TABLE 6

| Phase | Ingredient | Content (%) |
| --- | --- | --- |
| Water phase | Purified water | To 100 |
|  | Moisturizing ingredient | 10-25 |
|  | Thickener | Suitable amount |
|  | Metal ion sequestering agent | Suitable amount |
| Solubilized phase | PEG-60 hydrogenated castor oil | 0-2 |
|  | PEG-40 hydrogenated castor oil | 0-2 |
|  | Polyhydric alcohol | 0-10 |
|  | Flavoring | Suitable amount |
|  | Ethanol | 0-20 |
| Additional I | *Gynostemma pentaphyllum* gypenoside fraction | 0.20 |
| Additional II | Preservative | Suitable amount |
|  | Other additive | Suitable amount |

<Method for Preparing a Solubilized Formulation>

① Water and solubilized phases were evenly mixed and dissolved, respectively.

② The solubilized oil phase was inserted into the water phase and a resulting solution was mixed to get an oil-in-water emulsion.

③ An additional phase I, in which a *Gynostemma pentaphyllum* gypenoside fraction was dissolved, was solubilized and inserted into a resulting mixture and mixed together, after which an additional phase II was mixed therein together.

Experimental Example 4. Formulation Stability of a Cosmetic Composition

Cosmetic compositions of the above Formulation Examples 1, 2 and 3 were stored for 12 weeks under a condition of 4° C., 30° C., 45° C. and sunlight, and changes in color, odor and property of the formulation were observed through visual and sensory evaluations, which were indicated in Tables 7 to 9.

As shown in Tables 7 to 9, it was identified that the *Gynostemma pentaphyllum* gypenoside fraction had an excellent stability without any change in color, odor and property in a cosmetic composition state such as a high viscosity emulsified formulation, a low viscosity emulsified formulation and a solubilized formulation, even if it was stored for a long period of time under high temperature and sunlight conditions.

<Criteria for Stability Evaluation>
No change: ○
Slight change: Δ
Significant change: X

TABLE 7

| Elapsed time (week) | High viscosity emulsified formulation | | | | | | | | | | | |
|---|---|---|---|---|---|---|---|---|---|---|---|---|
| | Change in odor | | | | Change in color | | | | Change in formulation | | | |
| | 4° C. | 30° C. | 45° C. | Sunlight | 4° C. | 30° C. | 45° C. | Sunlight | 4° C. | 30° C. | 45° C. | Sunlight |
| 1 | ○ | ○ | ○ | ○ | ○ | ○ | ○ | ○ | ○ | ○ | ○ | ○ |
| 2 | ○ | ○ | ○ | ○ | ○ | ○ | ○ | ○ | ○ | ○ | ○ | ○ |
| 4 | ○ | ○ | ○ | ○ | ○ | ○ | ○ | ○ | ○ | ○ | ○ | ○ |
| 8 | ○ | ○ | ○ | ○ | ○ | ○ | ○ | ○ | ○ | ○ | ○ | ○ |
| 12 | ○ | ○ | ○ | ○ | ○ | ○ | ○ | ○ | ○ | ○ | ○ | ○ |
| Result | Stable | Stable | Stable | Stable | Stable | Stable | Stable | Stable | Stable | Stable | Stable | Stable |

TABLE 8

| Elapsed time (week) | Low viscosity emulsified formulation | | | | | | | | | | | |
|---|---|---|---|---|---|---|---|---|---|---|---|---|
| | Change in odor | | | | Change in color | | | | Change in formulation | | | |
| | 4° C. | 30° C. | 45° C. | Sunlight | 4° C. | 30° C. | 45° C. | Sunlight | 4° C. | 30° C. | 45° C. | Sunlight |
| 1 | ○ | ○ | ○ | ○ | ○ | ○ | ○ | ○ | ○ | ○ | ○ | ○ |
| 2 | ○ | ○ | ○ | ○ | ○ | ○ | ○ | ○ | ○ | ○ | ○ | ○ |
| 4 | ○ | ○ | ○ | ○ | ○ | ○ | ○ | ○ | ○ | ○ | ○ | ○ |
| 8 | ○ | ○ | ○ | ○ | ○ | ○ | ○ | ○ | ○ | ○ | ○ | ○ |
| 12 | ○ | ○ | ○ | ○ | ○ | ○ | ○ | ○ | ○ | ○ | ○ | ○ |
| Result | Stable | Stable | Stable | Stable | Stable | Stable | Stable | Stable | Stable | Stable | Stable | Stable |

TABLE 9

| Elapsed time (week) | Solubilized formulation | | | | | | | | | | | |
|---|---|---|---|---|---|---|---|---|---|---|---|---|
| | Change in odor | | | | Change in color | | | | Change in formulation | | | |
| | 4° C. | 30° C. | 45° C. | Sunlight | 4° C. | 30° C. | 45° C. | Sunlight | 4° C. | 30° C. | 45° C. | Sunlight |
| 1 | ○ | ○ | ○ | ○ | ○ | ○ | ○ | ○ | ○ | ○ | ○ | ○ |
| 2 | ○ | ○ | ○ | ○ | ○ | ○ | ○ | ○ | ○ | ○ | ○ | ○ |
| 4 | ○ | ○ | ○ | ○ | ○ | ○ | ○ | ○ | ○ | ○ | ○ | ○ |
| 8 | ○ | ○ | ○ | ○ | ○ | ○ | ○ | ○ | ○ | ○ | ○ | ○ |
| 12 | ○ | ○ | ○ | ○ | ○ | ○ | ○ | ○ | ○ | ○ | ○ | ○ |
| Result | Stable | Stable | Stable | Stable | Stable | Stable | Stable | Stable | Stable | Stable | Stable | Stable |

Experimental Example 5. Titer Stability of the Cosmetic Composition of the *Gynostemma pentaphyllum* Gypenoside Fraction within Formulation As shown in Formulation Examples 1, 2 and 3, cosmetic compositions of a high viscosity emulsified formulation, a low viscosity emulsified formulation and a solubilized formulation, respectively comprising 0.2% of the *Gynostemma pentaphyllum* gypenoside fraction, were stored under a condition of 4 CC, 30 CC, 45° C. and sunlight for 12 weeks and changes with passage of time (% compared to an initial content) in the gypenosides UL4 and UL5, which were index ingredients for quantification out of the *Gynostemma pentaphyllum* gypenoside ingredients, were observed through an HPLC analysis, and results thereof were indicated in Tables 10 to 12.

As shown in Tables 10 to 12, by experimentally identifying a content change of the gypenosides UL4 and UL5, which were index ingredients for quantification, it was identified that the *Gynostemma pentaphylium* gypenoside fraction had an excellent stability without any content decrease in a cosmetic composition state such as a high viscosity emulsified formulation, a low viscosity emulsified formulation and a solubilized formulation, even if it was stored for a long period of time under high temperature and sunlight conditions.

TABLE 10

| | High viscosity emulsified formulation (%) | | | | | | | |
|---|---|---|---|---|---|---|---|---|
| | Gypenoside UL4 | | | | Gypenoside UL5 | | | |
| Elapsed time (week) | 4° C. | 30° C. | 45° C. | Sunlight | 4° C. | 30° C. | 45° C. | Sunlight |
| 1 | 101.9 | 105.2 | 105.3 | 102.4 | 100.6 | 103.8 | 102.6 | 101.8 |
| 2 | 95.9 | 103.1 | 108.2 | 99.8 | 95.1 | 105.7 | 104.6 | 99.2 |
| 4 | 102 | 104.4 | 107.6 | 101.2 | 104.4 | 108.2 | 102.1 | 103 |
| 8 | 101.4 | 105.7 | 108.1 | 99.4 | 104.2 | 103.4 | 101.8 | 101.1 |
| 12 | 104.1 | 108.2 | 107.1 | 103.6 | 106.9 | 104.1 | 103.1 | 104.9 |
| Result | Stable | Stable | Stable | Stable | Stable | Stable | Stable | Stable |

TABLE 11

| Elapsed time | Low viscosity emulsified formulation (%) | | | | | | | |
|---|---|---|---|---|---|---|---|---|
| | Gypenoside UL4 | | | | Gypenoside UL5 | | | |
| (week) | 4° C. | 30° C. | 45° C. | Sunlight | 4° C. | 30° C. | 45° C. | Sunlight |
| 1 | 100.1 | 105.0 | 101.9 | 96.3 | 98.8 | 103.3 | 103.5 | 94.4 |
| 2 | 102.4 | 101.8 | 106.2 | 99.5 | 100.4 | 103.9 | 102 | 98.1 |
| 4 | 101.2 | 101.6 | 105.9 | 100.5 | 102.8 | 102.2 | 104.8 | 101.6 |
| 8 | 94.9 | 104.1 | 95.6 | 99.8 | 100.2 | 105.6 | 94.2 | 101 |
| 12 | 94.1 | 105.2 | 99.3 | 102 | 95.2 | 105 | 98.3 | 102.6 |
| Result | Stable | Stable | Stable | Stable | Stable | Stable | Stable | Stable |

TABLE 12

| Elapsed time | Solubilized formulation (%) | | | | | | | |
|---|---|---|---|---|---|---|---|---|
| | Gypenoside UL4 | | | | Gypenoside UL5 | | | |
| (week) | 4° C. | 30° C. | 45° C. | Sunlight | 4° C. | 30° C. | 45° C. | Sunlight |
| 1 | 98.8 | 100.0 | 102.8 | 98.8 | 98.8 | 100 | 100.3 | 97.9 |
| 2 | 91.9 | 103.2 | 101.6 | 94.8 | 95.7 | 105.1 | 101.4 | 95.9 |
| 4 | 98.7 | 102.7 | 94.2 | 98.4 | 105.1 | 108.6 | 97.2 | 104.9 |
| 8 | 97.6 | 98.5 | 97.2 | 98 | 102.8 | 103.7 | 102.1 | 103.5 |
| 12 | 99.5 | 104.5 | 94.9 | 94.6 | 102.3 | 104.9 | 95.6 | 103.3 |
| Result | Stable | Stable | Stable | Stable | Stable | Stable | Stable | Stable |

Experimental Example 6. Wrinkle-Reducing Effect of a Cream Comprising the *Gynostemma pentaphyllum* Gypenoside Fraction (Clinical Test)

To observe a wrinkle-reducing effect of a cream comprising the *Gynostemma pentaphyllum* gypenoside fraction, a cream comprising OA % of the *Gynostemma pentaphyllum* gypenoside fraction was prepared and a preparation composition thereof is such as that shown in a following Table 13.

TABLE 13

| Phase | Ingredient | Content (%) |
|---|---|---|
| Water phase | Purified water | To 100 |
| | Moisturizing ingredient | 10-25 |
| | Thickener | Suitable amount |
| | Metal ion sequestering agent | Suitable amount |
| Oil phase | PEG-100 Stearate | 0.1-2 |
| | Glyceryl Stearate | 0.1-2 |
| | Polysorbate 60 | 0.1-2 |
| | Stearic Acid | 0.1-2 |
| | Cetearyl Alcohol | 0.1-2 |

TABLE 13-continued

| Phase | Ingredient | Content (%) |
|---|---|---|
| | Capric/Caprylic Triglyceride | 10-30 |
| | Tocopheryl Acetate | 0.1-0.5 |
| Additional I | *Gynostemma pentaphyllum* gypenoside fraction | 0.40 |
| Additional II | Fragrance | Suitable amount |
| | Preservative | Suitable amount |
| | Other additive | Suitable amount |

An actual use test was carried out in order to evaluate an effect of cosmetics (high viscosity emulsified formulation) comprising the *Gynostemma pentaphyllum* gypenoside fraction prepared according to the composition of the above Table 13 on reducing a periorbital wrinkle, enhancing a skin elasticity and improving a skin dermal density. As a test subject, 20 women in their 30s to 60s having a periorbital wrinkle were supposed to use a test product (Formulation Example 1) and a control product (without comprising the *Gynostemma pentaphyllum* gypenoside fraction) on left and right sides of their facial regions respectively twice a day (morning/evening) after cleansing. Those women blindly used the test and control products for 12 weeks and each effect thereof was measured before use and in four, eight and twelve weeks after use.

1) Periorbital Wrinkle-Reducing Effect

Figure 5:
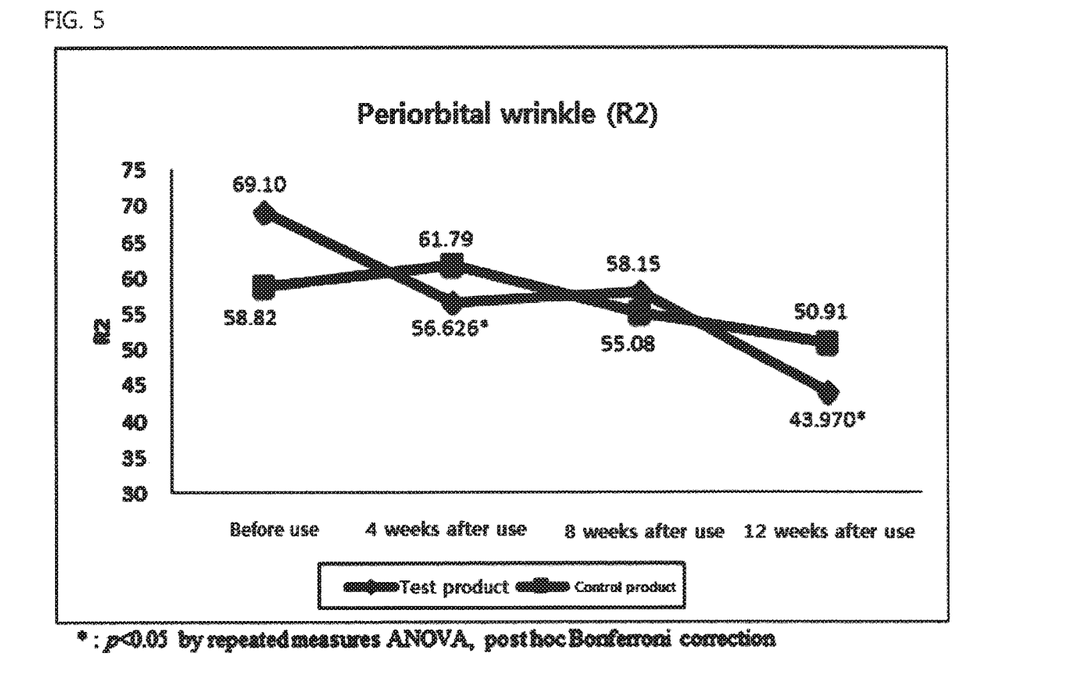
FIG. 5 shows a graph of clinical test results indicating an effect of the *Gynostemma pentaphyllum* gypenoside fraction on inhibiting a periorbital wrinkle.
Figure 6:
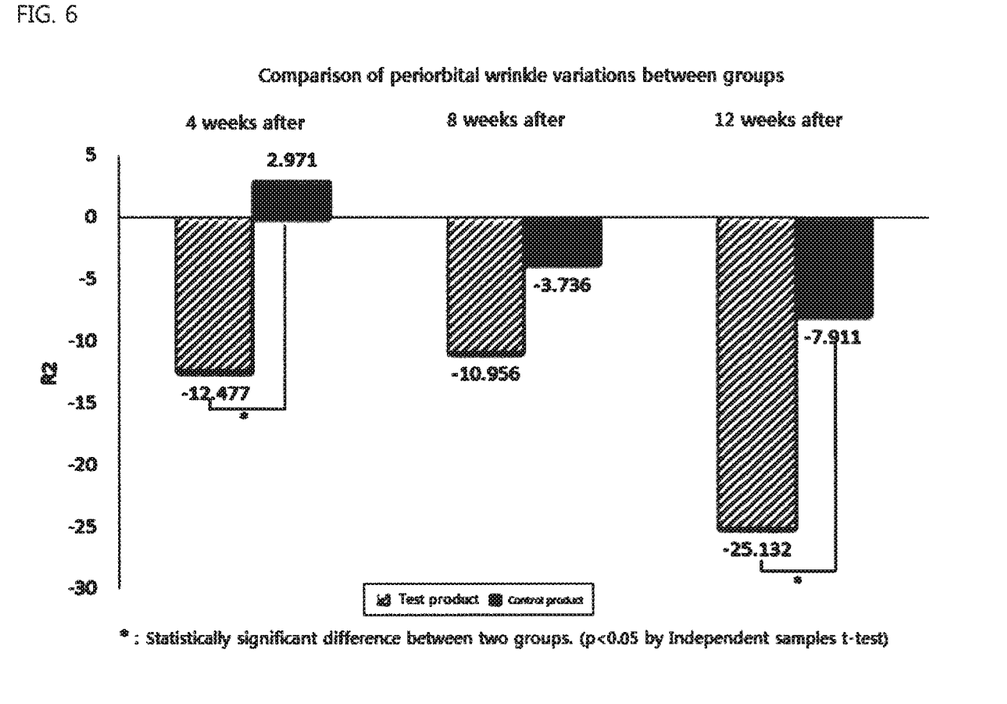
FIG. 6 shows a graph indicating a variation of a periorbital wrinkle depending on whether the *Gynostemma pentaphyllum* gypenoside fraction is applied or not.

A face is divided in half and a measurement was made on left and right regions 2 cm away from each tail end of eyes. As a measuring device, Visiometer SV600 (Courage-Khazaka electronic GmbH, Germany) was used to measure R2 (maximum roughness) out of wrinkle parameters, and results of a wrinkle-reducing effect were indicated in FIGS. 5 and 6. As a result of using the cream comprising the Gynostemma pentaphyllum gypenoside fraction for 12 weeks, it was identified that a region, in which the control product was used, did not show a periorbital wrinkle-reducing effect compared to before use, but a periorbital wrinkle on a region, in which the test product was used, was reduced from 69.10 to 43.97 (p<0.05).

2) Skin Elasticity-Enhancing Effect

Figure 7:
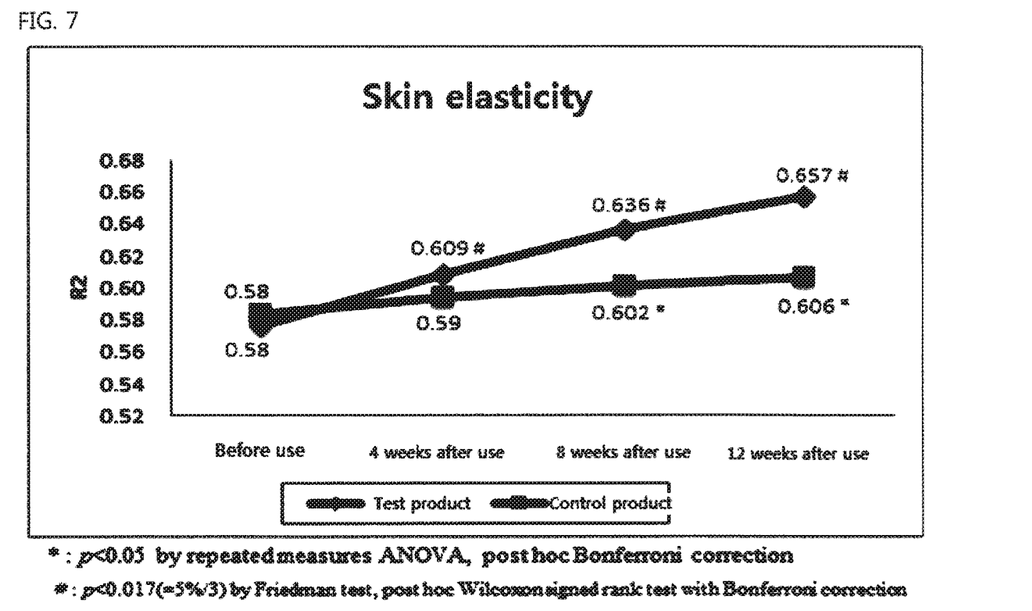
FIG. 7 shows a graph of clinical test results indicating an effect of the *Gynostemma pentaphyllum* gypenoside fraction on improving a skin elasticity.
Figure 8:
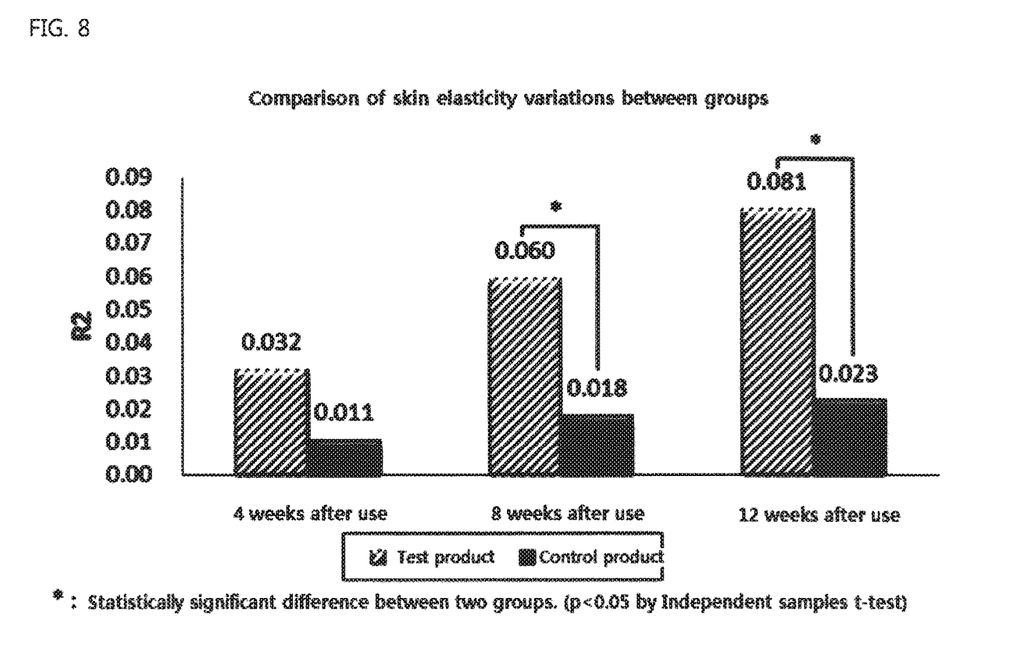
FIG. 8 shows a graph indicating a variation of a skin elasticity depending on whether the *Gynostemma pentaphyllum* gypenoside fraction is applied or not.

A skin elasticity was measured by means of Cutometer® (Courage+Khazaka electronic GmbH, Germany), and this measurement was made once on each of the same regions around both eyes, such that R2 (recovery of skin deformation) values were used as data to evaluate a degree of skin elasticity. An R2 value refers to a gross elasticity. The closer the value is to 1, the more elastic a skin is. Results of measuring a skin elasticity by means of use of the cream comprising the Gynostemma pentaphyllum gypenoside fraction were indicated in FIGS. 7 and 8. It was identified that a skin elasticity of a region, in which the test product was used, was increased up to 0.66 in 12 weeks after use in comparison with 0.58 before use, and was also significantly enhanced (p<0.05) in comparison with that of the region, in which the control product was used.

3) Skin Dermal Density-Improving Effect

Figure 9:
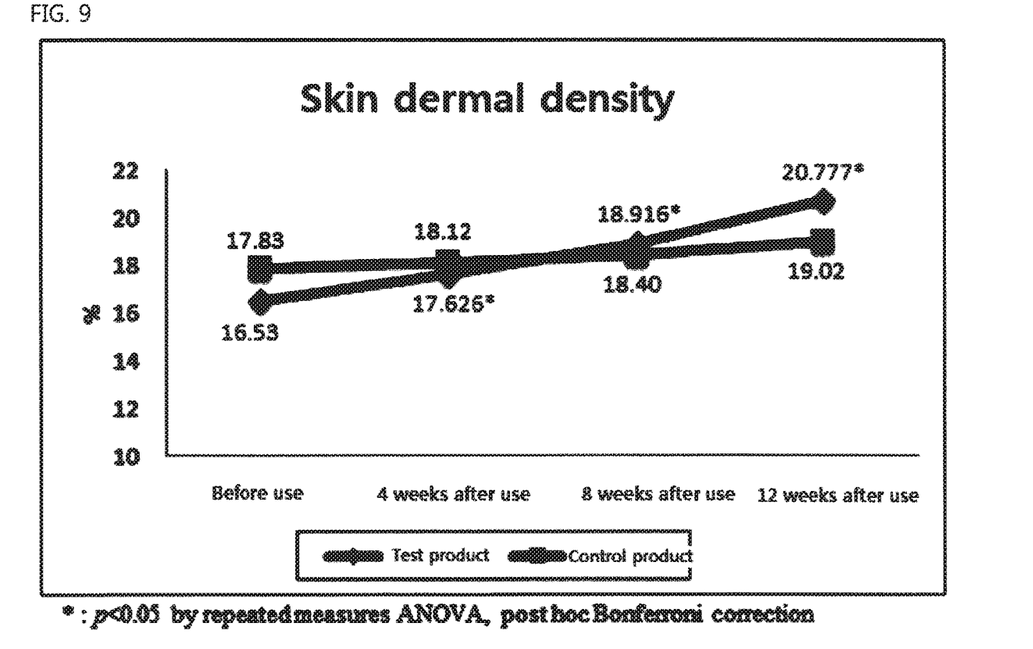
FIG. 9 shows a graph of clinical test results indicating an effect of the *Gynostemma pentaphyllum* gypenoside fraction on improving a skin dermal density.
Figure 10:
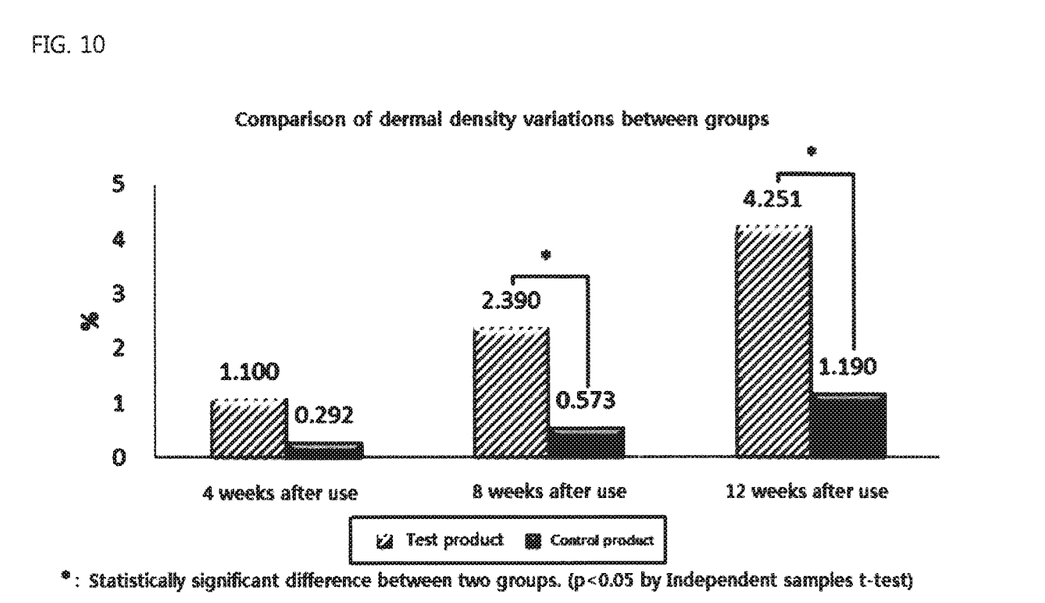
FIG. 10 shows a graph indicating a variation of a skin dermal density depending on whether the *Gynostemma pentaphyllum* gypenoside fraction is applied or not.

A skin dermal density was measured in such a way that regions around both eyes were photographed by means of Skin Scanner High Resolution Ultrasound (taberna pro medicum, Germany) and the measured images were used to analyze a skin dermal density before and after using products. A measurement unit of the skin dermal density was %, indicating that a higher measurement value means a more improvement in the dermal density. Results of measuring a skin dermal density-improving effect by means of use of the cream comprising the Gynostemma pentaphyllum gypenoside fraction were indicated in FIGS. 9 to 10. It was identified that a skin dermal density on the region, in which the control product was used, did not show a significant level of improvement in 12 weeks after use, but a skin dermal density on the region, in which the test product was used, was significantly improved in 12 weeks after use (20.78%) in comparison with before use (16.53%).

Experimental Example 7. Transparent Wrinkle-Reducing Effect

A clinical test on human skin was performed to identify a transparent wrinkle-reducing effect of the Gynostemma pentaphyllum gypenoside fraction.

The transparent wrinkle means that a sign of skin aging is observed inside a skin wrinkle along with an increase of age before a periorbital wrinkle is visibly formed around an eye, and the transparent wrinkle can be identified through a dermal density.

In this clinical test 10 adult women, who were judged to have the transparent wrinkle (those whose periorbital wrinkle reached zero based on global photodamage scores, having a low dermal density), were selected as a study subject and inclusion criteria were indicated in Table 14.

TABLE 14

| Severity | Wrinkle grading |
|---|---|
| 0 | None |
| 1 | none/mild |
| 2 | Mild |
| 3 | mild/moderate |
| 4 | Moderate |
| 5 | moderate/severe |
| 6 | Severe |
| 7 | very severe |

(Source: Br J Dermatol. 2010; 162(3): 497-502)

To observe a transparent wrinkle-reducing effect, a cream comprising 0.4% of the Gynostemma pentaphyllum gypenoside fraction was prepared and a preparation composition thereof is such as that shown in a following Table 15.

TABLE 15

| Phase | Ingredient | Content (%) |
|---|---|---|
| Water phase | Purified water | To 100 |
| | Moisturizing ingredient | 10-25 |
| | Thickener | Suitable amount |
| | Metal ion sequestering agent | Suitable amount |
| Oil phase | PEG-100 Stearate | 0.1-2 |
| | Glyceryl Stearate | 0.1-2 |
| | Polysorbate 60 | 0.1-2 |
| | Stearic Acid | 0.1-2 |
| | Cetearyl Alcohol | 0.1-2 |
| | Capric/Caprylic Triglyceride | 10-30 |
| | Tocopheryl Acetate | 0.1-0.5 |
| Additional I | Gynostemma pentaphyllum gypenoside fraction | 0.40 |
| Additional II | Fragrance | Suitable amount |
| | Preservative | Suitable amount |
| | Other additive | Suitable amount |

Selected subjects were supposed to apply the cream comprising 0.4% of the Gynostemma pentaphyllum gypenoside fraction on their facial regions twice a day (morning/evening) and changes in their dermal density on regions around both eyes were measured by means of Skin Scanner Heigh Resolution Ultrasound (taberna pro medicum, Germany) before application and in four weeks after application, results of which were indicated in Table 16. At that time, a rate of change in dermal density was calculated according to a following rate of change formula.

As shown in a following Table 16, a rate of change in dermal density was calculated when the cream comprising the Gynostemma pentaphyllum gypenoside was applied or not, thereby identifying whether the same reduced the transparent wrinkle or not.

<Rate of Change in Dermal Density>

Rate of change in dermal density (%) =

$$\frac{\text{Measured value after application} - \text{Measured value before application}}{\text{Measured value before application}} \times 100$$

TABLE 16

| No. | Age | Sex | Position | Dermal density (%) Before application | Dermal density (%) In four weeks after application |
|---|---|---|---|---|---|
| 1 | 29 | F | Left | 11.72 | 16.79 |
|   |    |   | Right | 12.93 | 14.21 |
| 2 | 26 | F | Left | 16.81 | 14.63 |
|   |    |   | Right | 15.51 | 14.31 |
| 3 | 25 | F | Left | 13.70 | 15.49 |
|   |    |   | Right | 11.91 | 16.82 |
| 4 | 34 | F | Left | 18.41 | 20.29 |
|   |    |   | Right | 17.61 | 19.27 |
| 5 | 28 | F | Left | 9.38 | 13.02 |
|   |    |   | Right | 9.45 | 10.02 |
| 6 | 33 | F | Left | 17.52 | 18.05 |
|   |    |   | Right | 15.86 | 17.46 |
| 7 | 32 | F | Left | 14.77 | 16.58 |
|   |    |   | Right | 18.41 | 20.25 |
| 8 | 30 | F | Left | 9.23 | 9.49 |
|   |    |   | Right | 10.64 | 15.82 |
| 9 | 26 | F | Left | 15.63 | 17.22 |
|   |    |   | Right | 16.88 | 19.56 |
| 10 | 25 | F | Left | 15.36 | 17.79 |
|    |    |   | Right | 16.56 | 17.89 |
| Average value |  |  |  | 14.41 | 16.25 |
| Standard deviation |  |  |  | 3.09 | 2.99 |
| Rate of change (%) |  |  |  |  | 12.77 (%) |

As a result, after using the cream comprising the *Gynostemma pentaphyllum* gypenoside fraction, it was found that a skin dermal density tended to increase as a whole and a rate of improvement in dermal density amounted to 12.8% on average. Thus, it could be identified that the transparent wrinkle, which was found in those in their 20s to early 30s, but invisible with naked eyes, was reduced as a whole.

The invention claimed is:

1. A method for reducing a wrinkle, comprising topically administering to a subject in need thereof a cosmetic composition comprising an effective amount of a *Gynostemma pentaphyllum* gypenoside fraction comprising 20 to 30 wt % of at least one of gypenoside UL4 and gypenoside UL5, wherein the gypenoside UL4 is (23ξ)-3β,20β,21α-trihydroxy-19-oxo-21,23-epoxy-dammar-24-ene-3-O-[α-L-rhamnopyranosyl (1→2)] [β-D-xylopyranosyl (1→3)]-α-L-arabinopyranoside; and wherein the gypenoside UL5 is (23ξ)-3β,20β,21α-trihydroxy-19-oxo-21,23-epoxy-dammar-24-ene-3-O-[α-L-rhamnopyranosyl (1→2)] [β-D-glucopyranosyl (1→3)]-α-L-arabinopyranoside.

2. The method of claim 1, wherein the effective amount of the *Gynostemma pentaphyllum* gypenoside fraction by 0.01 to 30 wt % compared to the total weight of the composition.

3. The method of claim 1, wherein the wrinkle is a transparent wrinkle.

* * * * *